United States Patent [19]

Yoshikawa

[11] 4,285,883

[45] Aug. 25, 1981

[54] PROCESS FOR PRODUCING 2-CHLORO-6-NITROBENZONITRILE

[75] Inventor: Hiroshi Yoshikawa, Fujioka, Japan

[73] Assignee: Nippon Kayaku Kabushiki Kaisha, Tokyo, Japan

[21] Appl. No.: 120,396

[22] Filed: Feb. 11, 1980

[30] Foreign Application Priority Data

Mar. 9, 1979 [JP]  Japan .................................. 54-26634

[51] Int. Cl.³ .......................................... C07C 121/52
[52] U.S. Cl. ................................................. 260/465 G
[58] Field of Search ................................... 260/465 G

[56] References Cited

U.S. PATENT DOCUMENTS

| 1,672,253 | 6/1928 | Giles | 260/465 R |
| 3,351,651 | 11/1967 | Rothman | 260/465 G |
| 3,644,471 | 2/1972 | Di Bella | 260/465 G |

*Primary Examiner*—Dolph H. Torrence
*Attorney, Agent, or Firm*—Wegner & Bretschneider

[57] ABSTRACT

Disclosed herein is a process for producing 2-chloro-6-nitrobenzonitrile by making reaction of 2,3-dichloronitrobenzene and an alkali cyanide in an aprotic solvent or in a basic solvent in the presence of cuprous chloride or in the presence of cuprous chloride and a cupric salt.

7 Claims, No Drawings

PROCESS FOR PRODUCING 2-CHLORO-6-NITROBENZONITRILE

DETAILED DESCRIPTION OF THE INVENTION

The present invention concerns a process for producing 2-chloro-6-nitrobenzonitrile characterized in that 2,3-dichloronitrobenzene is made to react with an alkali cyanide in the presence of cuprous chloride or in the presence of cuprous chloride and a cupric salt in an aprotic solvent or in a basic solvent. Hitherto, as a method for substituting a halogen atom of an aromatic halide with a cyano group, a method of making reaction of the aromatic halide with a metal cyanide in an aprotic solvent or in a basic solvent has been adopted in general. Hereupon, as an aprotic solvent, for instance, dimethylformamide, diethylformamide, dimethylsulfoxide, dimethylacetamide, formamide, N-methyl-2-pyrrolidone, hexamethylphosphoramide, etc. is used, and as a basic solvent, for instance, pyridine, picoline, quinoline, etc. is used. As a metal cyanide, for instance, cuprous cyanide, potassium ferrocyanide, potassium ferricyanide, copper ferrocyanide, palladium cyanide, etc. is used.

Concerning the method for producing 2-chloro-6-nitrobenzonitrile from 2,3-dichloronitrobenzene, a method by which 2,3-dichloronitrobenzene is made to react with cuprous cyanide in an aprotic solvent or in a basic solvent is described in British Pat. No. 861,898, German Pat. No. 1,143,803, Netherlands Pat. No. 104,318, etc.

The inventor, considering that the substitution of the chlorine atom by a metal cyanide such as cuprous cyanide not only requires an expensive reagent but also the recovery and be re-use of the metal after the reaction is difficult, has examined the substitution of the chlorine atom by cuprous chloride and an alkali cyanide both of which are inexpensive and easily recoverable to be re-used, and has found that the reaction proceeds also by these reagents as in the case of using the above-mentioned metal cyanide such as cuprous cyanide and then completed the present invention.

Of course the purified 2,3-dichloronitrobenzene is suitable for use in the process of the present invention, however, a mixture of 2,3- and 3,4-dichloronitrobenzenes which is discharged from the bottom of a distillation tower where 3,4- dichloronitrobenzene is distilled from the by-produced 2,3-dichloronitrobenzene in cases of nitration of o-dichlorobenzene is also suitably used. That is, on using about an equimolar amount of an alkali cyanide to 2,3-dichloronitrobenzene in the above-mentioned mixture of 2,3- and 3,4-dichloronitrobenzenes in the reaction of the mixture and the alkali cyanide in the presence of cuprous chloride, only 2,3-dichloronitrobenzene is practically subjected to the substitution with cyano group and 3,4-dichloronitrobenzene is recovered without being substituted.

The solvent for use in the present invention is, as in the conventional case of the substitution with the cyano group by cuprous cyanide, an aprotic solvent such as dimethylformamide, diethylformamide, dimethylsulfoxide, dimethylacetamide, formamide, N-methyl-2-pyrrolidone, hexamethylphosphoramide, etc. or a basic solvent such as pyridine picoline, quinoline, etc. The amount of the solvent mentioned above used in the reaction differs according to the kind of the solvent, however, it is preferable to use in an amount of 1 to 300% by weight of the amount of 2,3-dichloronitrobenzene, and more preferable, particularly to use 1 to 20% by weight.

According to the inventor's experience, it is more advantageous to use cuprous chloride coexisting with a cupric salt from the view point of reaction velocity, etc. In the process of the present invention, the amount of cuprous chloride or the sum of cuprous chloride and the cupric salt is preferably in the range of 0.05 to 1.0 mole per mole of 2,3-dichloronitrobenzene and from the consideration of the recovery and re-use of copper, 0.1 to 0.5 mole per mole of 2,3-dichloronitrobenzene is particularly suitable. The ratio of the cupric salt when cuprous chloride and the cupric salt are used together is preferably less than 70 mole% of the sum of the amounts of both salts, particularly more preferably 0.5 to 30 mole%. As the cupric salt, a conventional salt, for example, cupric sulfate, cupric nitrate, cupric chloride, cupric acetate, etc. is used. The once used copper is possibly recovered and re-used by recovering the inorganic matters, dissolving copper in the recovered matter in, for example, hydrochloric acid and then recovering the dissolved copper as cuprous chloride according to usual methods.

As the alkali cyanide, for example, sodium cyanide, potassium cyanide, etc. is possibly used. The amount of the alkali cyanide used in the process of the present invention is not particularly limited, however, the use of 0.5 to 1.5 mole per mole of 2,3-dichloronitrobenzene is preferable.

The temperature and the time period of the reaction depend upon the kind and amount of the solvent used in the reaction, however, usually a temperature of 100 to 220° C. is preferable, particularly, more preferable temperature is 140° to 200° C. The time period of the reaction is suitably from 1 to 15 hours.

The followings are the more detailed explanation while referring to Examples not limiting the scope of the present invention:

EXAMPLE 1

2,3-dichloronitrobenzene (19.2 g), cuprous chloride (2.4 g), anhydrous cupric sulfate (1.0 g), sodium cyanide (purity of 90%, 5.4 g) and dimethylformamide (3.0 g) were heated together to 190° C. and made to react for 3.5 hours at the temperature. After the reaction was over, 100 ml of dichloroethane were added to the reaction mixture and the mixture was filtered. After separating the filtrate, 100 ml of an aqueous 5% solution of ammonia were added to the filtrate and after well shaking the mixture, it was separated into layers. After distilling off dichloroethane from the organic layer and washing the residue with ethanol, 14.3 g of 2-chloro-6-nitrobenzonitrile was obtained as a pale yellow crystal. The yield was 78% theoretical.

EXAMPLE 2

Sixty grams of a mixture comprising 44.2% by weight of 2,3-dichloronitrobenzene and 55.8% by weight of 3,4-dichloronitrobenzene, 4.1 g of green-coloured cuprous chloride containing 20% by weight of cupric chloride, 7.5 g of 90%-pure sodium cyanide and 4.0 g of N-methyl-2-pyrrolidone were heated together to a temperature of 180° C. and made to react for 8 hours at the temperature. One hundred milliliters of dichloroethane were added to the reaction mixture and after filtering the mixture, 100 ml of an aqueous 5% solution of ammonia were added to the filtrate and after well agitating the thus separated resinous material was filtered off, and the filtrate was separated into layers. After distilling off dichloroethane from the organic layer, 100 ml of ethanol were added to the distillation residue to separate a crystalline substance. The substance was 2-chloro-6-nitrobenzonitrile weighing 17.8 g, the yield being 71% theoretical. By gaschromatographic analysis, it was found that the mother liquor contained 2.2 g of 2-chloro-6-nitrobenzonitrile, 3,4-dichloronitrobenzene and a small amount of unreacted 2,3-dichloronitrobenzene.

EXAMPLE 3

Sixty grams of a mixture comprising a 44.2% of 2,3-dichloronitrobenzene and 55.8% of 3,4-dichloronitrobenze, 4.1 g of newly purified cuprous chloride, 7.5 g of 90%-pure sodium cyanide and 4 g of dimethylformamide were heated together to a temperature of 190° C., and made to react for 5 hours at the temperature. After adding 200 ml of dichloroethane to the reaction mixture and filtering the mixture, the filtrate was examined by gaschromatography to find that the filtrate contained 20.4 g of 2-chloro-6-nitrobenzonitrile corresponding to a yield of 81% theoretical.

EXAMPLE 4

The same composition of the raw materials as in Example 2 except for containing 2 g of pyridine instead of 4.0 g of N-methyl-2-pyrrolidone was heated to a temperature of 190° C. and was made to react for 3.5 hours at the temperature. After treating the reaction mixture by the same procedures as in Example 3 and examining by gaschromatography, it was found that the filtrate thus obtained contained 17.7 g of 2-chloro-6-nitroenzonitrile corresponding to the yield of 70.2% theoretical.

What is claimed is:

1. A method of producing 2-chloro-6-nitrobenzonitrile which comprises contacting 2,3-dichloronitrobenzene with an alkali cyanide in an aprotic or basic solvent in the presence of (a) cuprous chloride; and a cupric salt selected from the group consisting of cupric sulfate, cupric nitrate, cupric chloride and cupric acetate.

2. A method of claim 1 wherein said solvent is present in an amount of from 1 to 20% by weight of the 2,3-dichloronitrobenzene.

3. A method of claim 1 or 2, wherein said solvent is aprotic.

4. A method of claim 1, wherein the total amount of cuprous chloride and cupric salt is 0.05 to 1.0 mol per mol 2,3-dichloronitrobenzene.

5. A method of claim 4, wherein said cupric salt is present in an amount of from 0.5 to 30 mol% of the sum of the cuprous chloride and said cupric salt.

6. A method of claim 1, which is conducted at a temperature of from 100 to 200° C.

7. A method of producing 2-chloro-6-nitrobenzonitrile which comprises contacting 2,3-dichloronitrobenzene with sodium cyanide in N-methyl-2-pyrrolidone in the presence of cuprous chloride and cupric oxide.

* * * * *